United States Patent
Inui et al.

(10) Patent No.: US 6,265,227 B1
(45) Date of Patent: Jul. 24, 2001

(54) METHOD FOR ASSAYING ANTIGEN RELATED TO DISORDERS CAUSED BY MENTAL STRESS

(75) Inventors: Takako Inui; Masashi Nakagawa; Yoshitake Terano; Mamiko Ozaki, all of Osaka (JP)

(73) Assignee: Suntory Limited, Osaki (JP)

( * ) Notice: Subject to any disclaimer, the term of this patent is extended or adjusted under 35 U.S.C. 154(b) by 0 days.

(21) Appl. No.: 09/043,703

(22) PCT Filed: Sep. 25, 1996

(86) PCT No.: PCT/JP96/02747

§ 371 Date: Jul. 21, 1998

§ 102(e) Date: Jul. 21, 1998

(87) PCT Pub. No.: WO97/12243

PCT Pub. Date: Apr. 3, 1997

(30) Foreign Application Priority Data

Sep. 26, 1995 (JP) .................................................... 7-247788
Oct. 20, 1995 (JP) .................................................... 7-273034

(51) Int. Cl.[7] ........................ G01N 33/566; G01N 33/543
(52) U.S. Cl. ........................ 436/501; 436/512; 436/543; 436/544; 436/545; 436/546; 436/547; 436/548; 436/811; 435/7.1; 435/7.7; 435/7.8; 435/7.9; 435/7.92; 435/7.93; 435/7.94; 435/7.95
(58) Field of Search .................................. 436/512, 501, 436/543–548, 811; 435/7.1, 7.7–7.9, 7.92–7.95

(56) References Cited

FOREIGN PATENT DOCUMENTS

WO94/15578 * 7/1994 (WO) .............................. A61K/7/16

OTHER PUBLICATIONS

Nakagawa et al., "Change of Taste Acceptability Owing to Mood State", The Japanese Journal of Taste and Smell Research, vol. 3, 1994, pp. 340–343.

Spielman, A.I., "Interaction of Saliva and Taste", Journal of Dent. Res., 69(3), Mar. 1990, pp. 838–843.

Glendinning, John I., "Effect of Salivary Proline–Rich Proteins on Ingestive Responses to Tannic Acid in Mice", Chemical Senses, vol. 17, No. 1, 1992, pp. 1–12.

Schmale et al., "Possible Role for Salivary Gland Protein in Taste Reception Indicated By Homology to Lipophilic–Ligand Carrier Proteins", Nature, vol. 343, 1990, pp. 366–369.

* cited by examiner

Primary Examiner—Long V. Le
Assistant Examiner—Pensee T. Do
(74) Attorney, Agent, or Firm—Pillsbury Winthrop LLP

(57) ABSTRACT

The invention relates to the development of a method for assaying an antigen which is associated with disorders caused by mental stress in a human body fluid by way of an immunoassay technique which utilizes an antibody against a mental stress related protein having the following properties or a fragment thereof:

(1) having a molecular weight of about 14 kDa (measured by SDS-PAGE); and (2) having the N-terminal partial sequence represented by SEQ ID NO: 1; and a kit for diagnosing disorders caused by mental stress which contains the above-mentioned antibody or a fragment thereof. Thus, the accumulation of mental stress can be easily estimated and judged and the results can be applied to the diagnosis of disorders caused by mental stress.

7 Claims, 2 Drawing Sheets

SEQUENCE LISTING

```
<160> NUMBER OF SEQ ID NOS: 1

<210> SEQ ID NO 1
<211> LENGTH: 28
<212> TYPE: PRT
<213> ORGANISM: Homo sapiens
<220> FEATURE:
<221> NAME/KEY: UNSURE
<222> LOCATION: (22)
<223> OTHER INFORMATION: 28 amino acid residues from the N-terminus of
<223> excised target protein

<400> SEQUENCE: 1

Ser Ser Ser Lys Glu Glu Asn Arg Ile Ile Pro Gly Gly Ile Tyr Asp
  1               5                  10                  15

Ala Asp Leu Asn Asp Xaa Trp Val Gln Arg Ala Leu
            20                  25
```

METHOD FOR ASSAYING ANTIGEN RELATED TO DISORDERS CAUSED BY MENTAL STRESS

BACKGROUND OF THE INVENTION

This invention relates to the diagnosis of disorders caused by mental stress. More specifically, it relates to a method for assaying an antigen related to disorders caused by mental stress in a human body fluid sample by an immunoassay technique with the use of an antibody or fragment thereof raised against a protein related to mental stress which is secreted under mental stress, and a diagnostic kit for said method.

In general, stress is a cause of fatigue, insomnia, uneasiness, irritation, and anxiety, etc. The term "stress" refers to a state wherein an individual is placed under physical or mental pressure. External and internal factors causing stress include:

(1) physicochemical factors such as cold, heat, noise and hypoxia:

(2) biological factors such as starvation, fasting vitamin deficiency, hard physical labor and pregnancy; and (3) psychological and social factors such as family problems, occupational problems, poor living conditions, problematic personal relations and financial problems. In contemporary society, stress caused by psychological and social factors is an extremely serious problem.

According to "DSM-III-R (Diagnostic and Statistic Manual for Mental Disorders)" published by the U.S. Psychiatric Society, for example, intensities of psychological and social stress are differentiated as transient or persistent phenomena. Stress arising from social or psychological factors is also differentiated as pertaining to children, adolescents or adults. On the basis of such criteria, the type and intensity of stress can be roughly evaluated and based on the evaluation a therapeutic schedule, crisis intervention or other assistance strategy can be determined. Stress caused by transient phenomena tends to be readily apparent as the factors leading to the condition are easy to observe. In contrast, mental stress resulting from persistent phenomena is often overlooked. Such long term stress can constitute an etiololgy of stress related disease.

However, it can take a time to give a definitive diagnosis of stress as a causative factor in disease since standards for the diagnosis of mental stress vary. Therefore, it will be of great benefit to be able to diagnose an accumulation of mental stress efficiently and easily.

The present inventors performed a sensory evaluation of taste perception over a period of time by using a computerized time-intensity on-line system and subsequently reported that sensitivity to bitterness is lowered under mental stress [Mizuma et al., "the Japanese Journal of Taste and Smell Research", Vol. 3: 340–343, 1994]. Namely, it is reported that, when an aqueous solution of quinine, i.e., a bitter substance, is held in the mouth in a mentally stressed state, perception of bitterness is reduced and any aftertaste lasts for a shortened period of time. That is to say, subjects under mental stress are less sensitive to bitter substances in the mouth.

Although in daily life most people experience changes in taste sensitivity due to physical or psychological conditions, few attempts have been made to clarify the reasons therefor. For example, A. I. Spielmam reports that after hard exercise, the buffer action of the saliva is enhanced and, this accounts for the reason why sensitivity to sourness is reduced (Journal of Dent. Res., 69:838–843, 1990).

With respect to substances reducing bitterness or a sensitivity to bitterness, there have been known proline rich proteins (PRPs) which are contained in the saliva and regulate the bitterness of tannic acid (J. I. Glendinning, Chem. Sens., 17:1–12, 1992). It is also reported that VEG protein secreted from von Ebner's glands in the oral cavity has a function of transporting fat-soluble substances to taste sensitive organs (H. Schemale et al., Nature 343:366–369, 1990). However, there have been no reports about the relation between these substances and stress so far.

SUMMARY OF THE INVENTION

It is an object of the present invention to develop a method whereby the accumulation of mental stress can be easily estimated and judged and to apply this method to the diagnosis of disorders caused by mental stress.

To achieve the above-mentioned object, the present inventors have conducted extensive studies. As a result, they have found that a specific protein capable of lowering sensitivity to bitterness is produced in the saliva under prolonged mental stress due to persistent exercise and that this protein contained in a human body fluid can be assayed with the use of a suitable antibody, thus enabling the present invention to be completed.

DETAILED DESCRIPTION OF THE INVENTION

Figure 3:
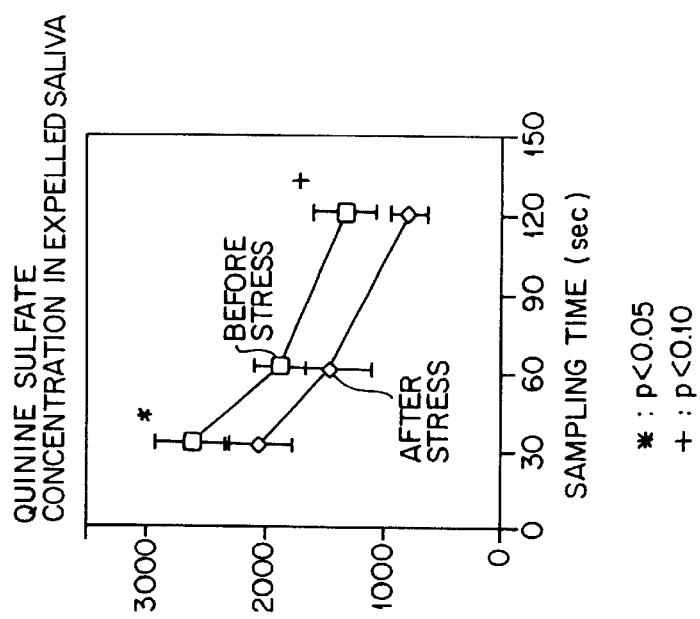
FIG. 3 shows the quinine sulfate concentrations in saliva expelled following exposure to mental stress.

The present invention provides a method for assaying an antigen related to disorders caused by mental stress in a human body fluid by an immunological technique using an antibody or a fragment thereof against the mental stress-related protein having the following properties:

(1) having a molecular weight of about 14 kDa (measured by SDS-PAGE); and (2) having the N-terminal partial sequence represented by SEQ ID NO: 1.

The mental stress-related protein employed for obtaining the antibody to be used in the method of the present invention is one separated and purified from the saliva of human subject under mental stress by the methods as will be described hereinafter. It has been proved that this protein is one having a molecular weight of about 14 kDa when measured by SDS-PAGE. The band of this protein is excised and sequenced by using a protein sequencer (ABI473A manufactured by Applied Biosystems Japan) to give the N-terminal amino acid sequence represented by SEQ ID NO: 1.

The antibody against the mental stress-related protein to be used in the present invention can be produced by immunizing an animal such as rabbit, rat, goat, sheep or mouse with the above-mentioned protein related to mental stress by a method well known by those skilled in the art. Alternatively, use can be made of a mental stress-related protein which has been synthesized by the solid synthesis method, etc. or one obtained by gene recombination techniques.

The antibody may be either polyclonal or monoclonal. These antibodies can be produced by methods well known by those skilled in the arts. In the method of the present invention, it is also possible to use binding fragments of the monoclonal or polyclonal antibody, for example, Fab, $F(ab')_2$ and Fv fragments. These antibody fragments can be obtained by digesting a complete antibody with papain, pepsin, etc. in the conventional manner.

The immunological-assay technique used in the present invention is exemplified by radioimmunoassay, enzyme immunoassay, immunofluorescence assay, light emission immunoassay, immunoprecipitation and immunoturbidimetry. Among all, enzyme immunoassay, in particular, enzyme-linked immunosorbent assay (ELISA) is appropriately used in hospitals, etc., since the mental stress-related protein can be detected with high sensitivity and a number of specimens can be automatically assayed thereby.

In the ELISA method, an antibody, preferably a monoclonal antibody, or a fragment thereof against the mental stress-related protein is first immobilized on a carrier as a primary antibody. Preferred carrier is a solid carrier, such as an ELISA plate container molded from a carrier polymer such as styrene or polystyrene. The monoclonal antibody or its fragment can be immobilized by, for example, dissolving the monoclonal antibody or its fragment in a buffer such as a carbonate buffer or a borate buffer followed by the adsorption onto the carrier.

Separately, an antibody (a monoclonal antibody or a polyclonal antibody, or a fragment thereof) used as the secondary antibody is labeled preferably with a non-radioactive label. Enzyme labels, fluorescent labels, light emission labels, etc. can be used as the non-radioactive label. It is preferred that an enzyme label such as alkaline phosphatase, β-galactosidase or horse radish peroxidase be used.

Although the body fluid to be used in the assay of the present invention is not particularly limited, saliva is preferred, since the mental stress-related protein is secreted in a large amount into the saliva under mental stress.

The disorders caused by mental stress which can be diagnosed by the method of the present invention are those caused by psychological and social factors such as family problems, occupational problems, living circumstances, personal relations and financial problems, from among various external and internal factors causing the stressed state as described above.

The present invention further provides a diagnostic kit for the diagnosis of disorders caused by mental stress which contains an antibody against the mental stress-related protein or a fragment thereof. When two monoclonal antibodies are employed, for example, the kit contains a carrier having a monoclonal antibody against the mental stress-related protein immobilized thereon, or a monoclonal antibody against said protein and a carrier for immobilizing the same, and the other monoclonal antibody which has been labeled. This kit may further contain a calibration curve, a manual for handling standard solutions, etc.

To further illustrate the present invention in greater detail, and not by way of limitation, the following Referential Example and Examples will be given.

REFERENTIAL EXAMPLE 1

Indication of Mental Stress

After imposing a long-lasting, stressful exercise on subjects, changes in sensitivity to bitterness thus caused were measured and employed as an indication of mental stress.

Figure 1:
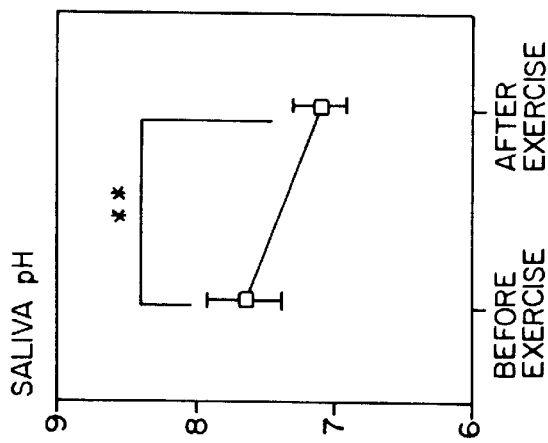
FIG. 1 shows changes in the pH value of saliva under mental stress.

The exercise, in which the subjects counted specified letters in character strings given on a computer display and input answers, was continued for 40 minutes. After completion of the exercise, the subjects suffered mental exhaustion, which was also indicated by physiological analysis such as a decrease in the pH value of the saliva in the oral cavity and a decrease in GSR (galvanic skin resistance) (FIG. 1).

Figure 2:
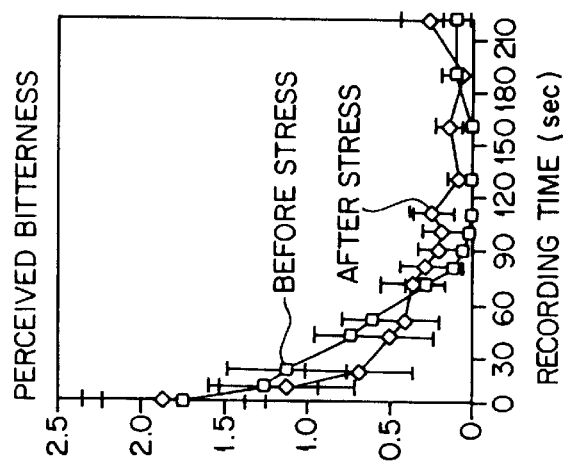
FIG. 2 shows the intensities of perceived bitterness of quinine sulfate before and after exposure to mental stress.

Before and after the exercise, perception of bitterness produced by 13.6 ppm of quinine sulfate (perceived bitterness) was evaluated by each subject in the following manner. Namely, 10 ml of a quinine sulfate solution was held in the mouth and the intensity of perceived bitterness was recorded on an evaluation sheet. Then the solution was expelled and the perceived aftertaste of bitterness was evaluated for 210 seconds at intervals of 10 or 30 seconds (FIG. 2). At the same time, the saliva was sampled 30, 60 and 120 seconds after expelling the bitter solution and the quinine sulfate concentrations in these samples were measured in the following manner. The sampled saliva was diluted with distilled water and then subjected to HPLC on ODS-AM150×46 mm (fluorescent wavelength: Ex. 252 nm; Em. 382 nm, solvent: 80% MeOH, flow rate: 1.0 ml). As a result, five subjects reported a tendency to feel a decrease in the bitterness after the completion of the exercise. At the same time, quinine sulfate concentration in the saliva was also lowered, thus suggesting a relation to the intensity of perceived bitterness (FIG. 3). Based on these results, changes in sensitivity to bitterness were employed as an indication of the mental stress.

EXAMPLE 1

Production of Protein Due to Mental Stress

Figure 4:
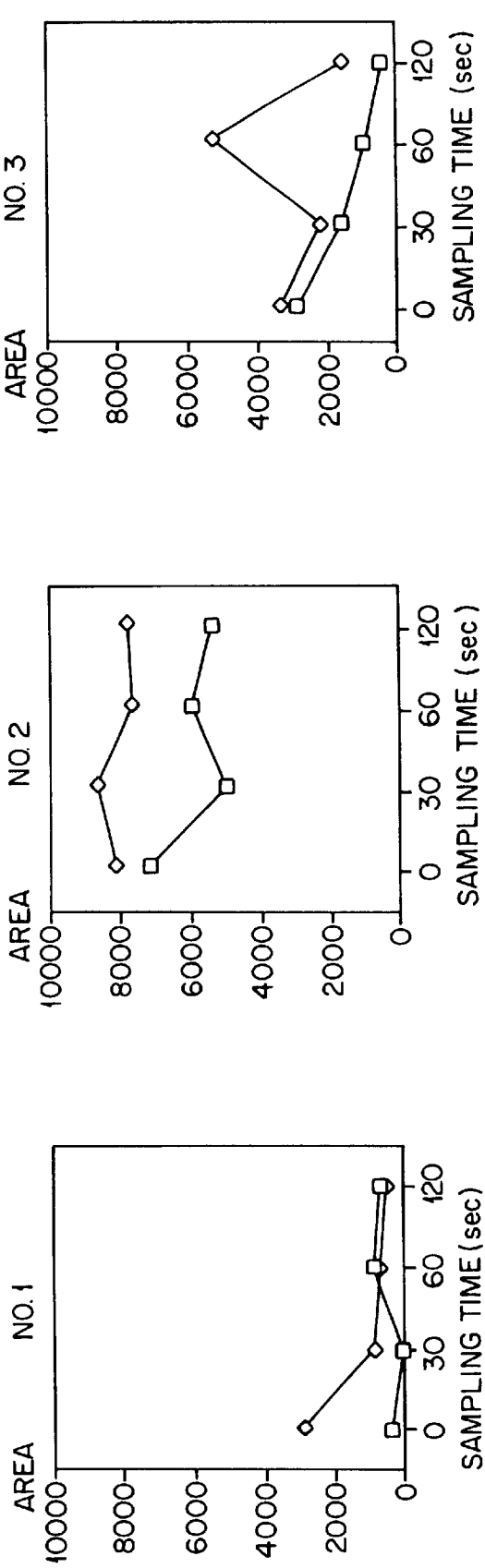
FIG. 4 (No.1–No.5) shows the results of the determination of quantity of the mental stress-related protein in saliva before and after exposure to mental stress.
Figure 4:
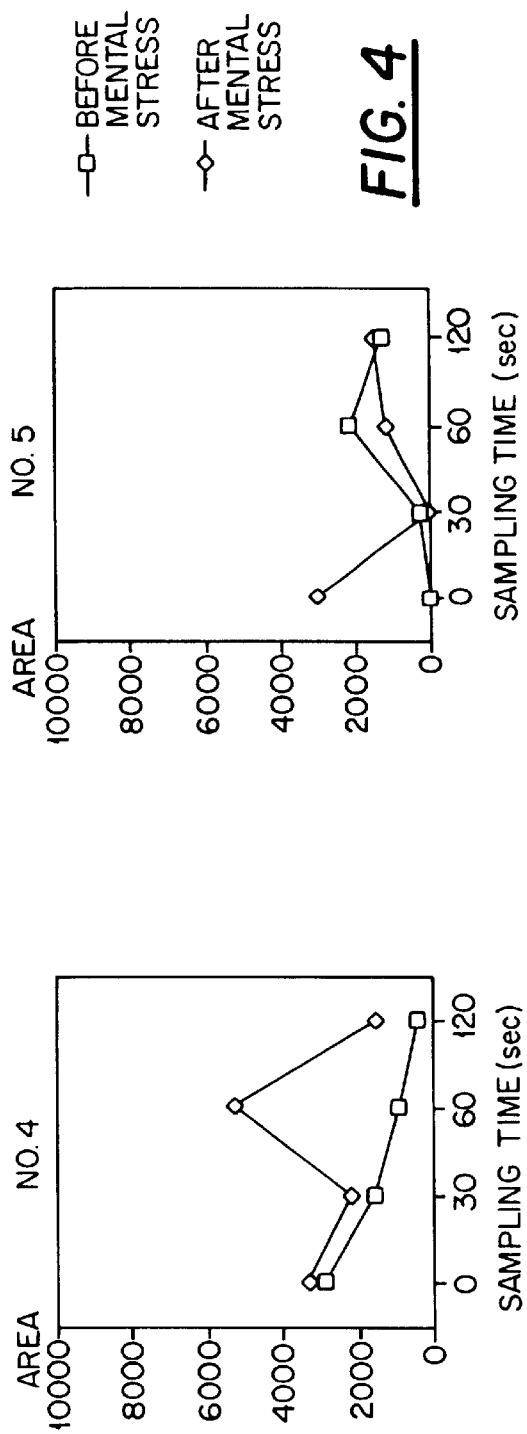

SDS-electrophoresis was performed on the saliva samples, which were collected from five subjects when they were at rest; immediately after practicing the exercise (0 second); and 30, 60 and 120 seconds after expelling the bitter solution in the evaluation of the bitter solution before and after practicing the exercise. To elevate the solubility of the protein, 3 μl of a sample buffer (0.0625 M Tris-HCl, 10% of glycerol, 5% of β-mercaptoethanol and 2.3% of SDS) was added to 10 μl of each saliva sample. After being allowed to react at 37° C. for 30 minutes, the sample was electrophoresed on SDS-PAGE (15% separation gel). The electrophoresis was performed for about 60 minutes by using an electrode buffer (3.03% of Tris, 14.4% of glycerol and 1% of SDS) on a 30 mA/1 plate (6.5×9 cm$^2$). After the completion of the electrophoresis, the gel was silver stained in the following manner. Namely, the gel plate was placed in the mixture of 50% methanol and 10% acetic acid for 30 minutes, then by the mixture of 5% methanol and 7% acetic acid for 30 minutes or longer. After being washed with distilled water for 15 minutes three times, the gel was treated successively with 5 g/ml of DDT for 30 minutes and 0.1% of AgNO$_3$ for 30 minutes. Next the gel plate was lightly washed with distilled water, then treated with Developer (containing 107 μl of formaldehyde and 6 g of Na$_2$CO$_3$ plus distilled water to make up 200 ml) and 5 ml of 2.3 M citric acid for 5 minutes, and washed with distilled water again. As a result it was found that a band appearing at around 14 kDa showed an obvious difference in concentration before and after exposure to the exercise. Each of the saliva samples collected 0, 30, 60 and 120 seconds after the exercise showed a difference in concentration of this band. The largest difference was observed between the saliva sample collected at rest and the one collected immediately after the exercise (0 second). That is, the latter sample showed the highest concentration. This data was processed to provide a chromatogram with the use of a densitometer (CS-9000, manufactured by Shimadzu Corporation) and the peak areas around 14 kDa, at which remarkable changes in concentration were observed, were compared. FIG. 4 shows the results. The difference in the concentration of this band lessened with the passage of time after the exercise. Therefore, it is assumed that the protein shown by this band is a specific protein which is produced within a short period of time due to mental stress and thus is available as an indication of mental stress.

EXAMPLE 2
Method of the Isolation of the Mental Stress-Related Protein and its Amino Acid Sequence To saliva samples collected before and after the exercise was added a sample buffer (4.65 mM of sodium barbiturate hydrochloride and 10% of glycerol, pH 6.8) to give a concentration of about 25% by volume and the obtained samples were incubated at 37° C. for 30 minutes.

Next, these samples were subjected to SDS-PAGE electrophoresis with the use of a separation gel [7.5% of acrylamide (Bis 1.2%), a running gel buffer (91.1 mM of sodium barbiturate hydrochloride, pH 8.9), 10% of APS, 1% of TMEMD], a concentration gel [5% of acrylamide (Bis 1.2%), stacking gel buffer (9.3 mM of sodium barbiturate hydrochloride, pH 6.7) and an electrode buffer (41.1 mM of sodium barbiturate/glycerol, pH 8.3).

After completion of the electrophoresis, the proteins were blotted onto a PVDF membrane. Then the membrane was divided into two halves and one of them was stained with CBB. The buffer used in the blotting contained 4.65 mM of sodium barbiturate/glycerol and 20% of MeOH.

Based on the results of the CBB-staining, the position of the band of the target protein was identified and the corresponding section was excised from the unstained half. Then the amino acid sequence of about 30 amino acid residues from the N-terminus of the excises band was read on a protein sequencer (ABI473A manufactured by Applied Biosystems Japan) to thereby give the N-terminal amino acid sequence represented by SEQ ID NO: 1.

EXAMPLE 3
Preparation of Antibody Against the Mental Stress-Related Protein
1) Preparation of Immunogen The protein related to mental stress was dissolved in PBS(−) to give a protein concentration of 1 mg/ml. The obtained solution was sterilized by being passed through a milipore filter (0.22 μm filter unit), pipetted into sterile tubes for freezing, then stored in a frozen state at −80° C. and thawed before using. In primary challenge, the solution was mixed with the same amount of complete Freund's adjuvant and used in the form of a water-in-oil type emulsion. In boosting, it was mixed with incomplete Freund's adjuvant and used in the form of a water-in-oil type emulsion.

2) Immunization of Animal

With respect to the immunization schedule, the primary challenge was followed by boosting three times at intervals of 1 week. Namely, the primary challenge was performed by injecting 0.2 mg/animal of the antigen into several parts of the food pads of two Japanese white rabbits (female) of the SPF (specific pathogen free) grade weighing 3.5 kg. Next, the rabbits were boosted by subcutaneous injections of 0.1 mg/animal of the antigen. On the other hand, 0.02 mg/animal of the antigen was subcutaneously and intraperitoneally injected into ten BALB/c mice (female) aged 6 weeks as the primary immunization. Next, these mice were boosted by intraperitoneal administrations of 0.01 mg/animal of the antigen. One week after the final immunization, 2×5×10$^6$/animal of Ehrlich tumor cells were intraperitoneally injected into the mice.

3) Separation of Serum or Ascitic Supernatant and Removal of Fat

In the case of the rabbits, the blood was sterilely collected 10 days after the final immunization from the ear central artery. After centrifuging, the serum was taken up and inactivated by heating at 56° C. for 30 minutes. In the case of the mice, the developed ascitic fluid was collected, centrifuged and the ascitic supernatant was recovered. In a centrifugal tube provided with a glass stopper, the ice-cooled serum or ascitic supernatant was mixed with ice-cooled trichloro-trifluoroethane at a ratio by volume of 3:2. After vigorously stirring and shaking, the mixture was treated with a refrigeraed centrifuge and the supernatant recovered.

4) Method for Purifying Antibody

The defatted serum (or ascitic supernatant) was mixed with the equal volume of saturated ammonium sulfate (pH 7.4) and centrifuged at a high speed. The fraction thus salted out was recovered and desalted through a Sephadex G25 column with the use of PBS(−). Next, the desalted matter was subjected to a column chromatography on DEAE and the IgG fraction was isolated and purified. The concentration was adjusted to 10 mg/ml with PBS(−), and the IgG was stored in a frozen state at −80° C.

5) Preparation of Rabbit IgGF(ab')$_2$

The rabbit IgG fraction was dialyzed against a 0.1 M acetate buffer (pH 4.3) and IgG was mixed with pepsin at a weight ratio of 50:1. The obtained mixture was reacted in a warm bath at 37° C. for 8 to 14 hours and then ice-cooled. The mixture was centrifuged at a high speed to remove the precipitate, and the supernatant was adjusted to pH 8.0 with 1 M NaOH. Finally, the IgGF(ab')$_2$ fragment was recovered by Sephadex G150 column chromatography.

6) Measurement of Antibody Titer

The mental stress-related protein was dissolved in 0.1 M carbonate/bicarbonate buffer (pH 9.5) and the concentration was adjusted to 0.001 mg/ml. Then the solution was added into a flat-bottomed 96-well microtiter plate at a ratio of 0.1 ml/well and allowed to stand at 37° C. for 1 hour. After the supernatant was discarded, the plate was washed with a washing solution [PBS(−) containing 0.1% of Tween-20]. Then a blocking solution [PBS(−) containing 0.1% of gelatin] was added at a ratio of 0.15 ml/well and the plate was allowed to stand at 37° C. for 30 minutes.

Separately, an antibody sample having a concentration of 1 mg/ml was prepared with a diluent [PBS(−) containing 0.1% of gelatin], and then serial antibody dilutions (×500, ×1000, ×2000, ×4000, ×8000, ×16000, ×32000 and ×64000) were prepared in a V shape-bottomed 96-well microtiter plate.

Then the above-mentioned plate having the protein related to mental stress adsorbed thereon was washed and the serial antibody dilutions were added to each well in duplicate series and the plate was allowed to stand at 37° C. for 1 hour. After washing the plate, a 1000-fold dilution of the biotinylated secondary antibody [i.e., biotinylated anti-rabbit Ig (Amersham cat No. RPN-1004) against the rabbit antibody, or biotinylated anti-mouse Ig (Amersham cat No. RPN-1001) against the mouse antibody] was added at a ratio of 0.1 ml/well and allowed to stand at 37° C. for 1 hour. After washing the plate, a 1000-fold dilution of enzyme-labeled avidin [i.e., avidin conjugated to a alkaline phosphatase (Dakopatts cat No. D365) or streptoavidin conjugated to an alkaline phosphatase (GIBCO BRL, cat No. 9542SA)] was added at a ratio of 0.1 ml/well and allowed to stand at 37° C. for 30 minutes. After washing, the substrate (2.5 mM disodium p-nitrophenylphosphate in 10 mM diethanolamine containing 0.5 mM of MgCl$_2$, pH 9.5) was added at a ratio of 0.1 ml/well and allowed to stand at room temperature in the dark. Next, a terminating solution (3 M aqueous solution of NaOH) was added at a ratio of 0.05 ml/well.

Then, the absorbance of the reaction mixture at 405 nm was measured with a microplate autoreader. The dilution rate of the antibody sample (1 mg/ml) (logarithmic scale) and the absorbance (normal scale) were plotted on a semi-logarithmic graph paper. The data of the samples were graphed in decreasing order of the dilution rate. The dilution rate corresponding to the midpoint of the linear region in the sigmoid curve showing the logarithmic change thus obtained was referred to as the antibody titer (Unit/mg). The antibody titer of the rabbit antibody IgGF(ab')$_2$ was calculated as 12,000 Unit/mg in the two lots, while that of the pooled mouse ascites fluid IgG was calculated as 8,000 Unit/mg.

7) Preparation of Biotinylated Antibody

By using biotinylated N-hydroxysuccinimide (BNHS), biotin was covalently bonded to mouse IgG. More specifically, 57 μl of a 0.1 M solution of BNHS in distilled dimethylformamide was added to 1 ml of a 10 mg/ml solution of mouse IgG in 0.1 M NaHCO$_3$. After reacting at 22° C. for 1 hour, the reaction mixture was dialyzed against 0.05 M PBS(−) (pH 7.2) at 4° C. for 24 hours. The dialyzate was replaced several times. After the completion of the dialysis, the equal volume of re-distilled glycerol was added thereto and the obtained mixture was stored in a frozen state.

8) Preparation of Alkaline Phosphatase (AP)-Labeled Antibody 5 mg of AP commercially available as a precipitate from saturated ammonium sulfate (alkaline phosphatase type VIIS, Sigma) was re-suspended in 0.2 ml of 0.1 M PBS(−) (pH 6.8) containing 1.25% of glutaraldehyde. After allowing to stand at 22° C. overnight, it was dialyzed against physiological saline and the volume was adjusted to 1 ml with physiological saline. Then 1 ml of 2.5 mg/ml mouse IgG and a 1 M carbonate buffer (pH 9.5) were added thereto and the obtained mixture was allowed to stand at 4° C. for 24 hours. After adding 10 μl of a 2 M lysine solution, the mixture was allowed to stand at 22° C. for 2 hours. 0.005 M PBS(−) (pH 7.2) was recovered and stored in a light shield container at 4° C.

9) Preparation of Alkaline Phosphatase (AP)-Labeled Avidin 5 mg of AP was activated by treating with glutaraldehyde in a similar manner as described in 7) and then mixed with avidin (Vector) at a molar ratio of 1:1. After reacting at 4° C. overnight, the reaction mixture was dialyzed against physiological saline at 4° C. overnight. Then bovine serum albumin (BSA) was added thereto to give a final concentration of 1% and the obtained mixture was stored in the dark.

EXAMPLE 4

Measurement by ELISA-Sandwich Technique

ELISA-Sandwich AP Technique

1) Preparation of Phosphate-Buffered Saline (PBS)

8.0 g of NaCl, 0.2 g of KCl and 0.24 g of KH$_2$PO$_4$ were dissolved in 800 ml of distilled water. After being adjusted to pH 7.2, the solution was filled up to a total volume of 1,000 ml.

2) Preparation of Plate having Antibody Absorbed Thereon

The rabbit IgGF(ab')$_2$ anti-stress-related protein was diluted with the PBS as prepared in above 1) to give a concentration of 0.02 mg/ml. Then the antibody solution was added to a flat-bottomed 96-well microtiter plate for ELISA (Costar cat No. 3590) at a ratio of 50 μl/well and allowed to stand at room temperature for 2 hours. Thus the antibody was bound to the plate at a ratio of about 100 ng/well (300 ng/cm$^2$).

3) After removing the antibody solution, the plate was washed twice with PBS. Then a blocking solution (PBS containing 1% of gelatin and 0.02% of NaN$_3$) was added at a ratio of 200 μl/well and allowed to stand at room temperature for 2 hours or longer overnight.

4) Preparation of Antigen Sample

15 μl of protein solubilizing solution (0.0625 M Tris-HCl containing 10% of glycerol, 5% of β-mercaptoethanol and 2.3% of SDS) was added to 50 μl of a saliva sample and the obtained mixture was allowed to stand at 37° C. for 30 minutes. Then it was centrifuged and the supernatant was recovered. On a V shape-bottomed 96-well microtiter plate (Costar cat No 3897), 8-serial dilutions ($1\times10^4$, $2\times10^4$, $4\times10^4$, $8\times10^4$, $16\times10^4$, $32\times10^4$, $64\times10^4$ and $128\times10^4$) of a control standard sample (1 mg/ml) and 4-serial dilutions ($1\times7.7$, $3\times7.7$, $9\times7.7$, $27\times7.7$) of the supernatant of the saliva treated with the protein solubilizing solution were prepared in a diluent (PBS containing 0.1% of gelatin, 0.02% of $NaN_3$ and 0.1% of Tween-20).

5) The plate of the above 3) was washed twice with a washing solution (PBS containing 0.02% of $NaN_3$ and 0.1% of Tween-20). Then the sample prepared in the above 3) was added thereinto in duplicate series at a ratio of 50 µl/well and allowed to stand at 37° C. for 1 hour.

6) After washing the plate, a 500-fold dilution of an enzyme-labeled secondary antibody (alkaline phosphatase-conjugated mouse IgG anti-stress-related protein antibody: 1 mg/ml) was added at ratio of 50 µg/well and allowed to stand at 37° C. for 1 hour.

7) After washing the plate, a substrate (2.5 mM of disodium p-nitrophenylphosphate in 10 mM of diethanolamine containing 0.5 mM of $MgCl_2$, pH 9.5) was added at a ratio of 50 µl/well. The plate was left to stand at room temperature in the dark for 10 minutes, and a reaction terminating solution (3 M aqueous solution of NaOH) was added at a ratio of 25 µl/well.

8) Then the absorbance of the reaction mixture at 405 nm was measured with a microplate autoreader.

9) The concentration of the control standard sample (1 mg/ml) (logarithmic scale) and the absorbance (normal scale) were plotted on a semilogarithmic graph paper to give a sigmoid curve. Saliva sample dilutions which give absorbances applicable to the linear region in the sigmoid curve were selected and the concentrations of the protein in the dilutions were determined. The values thus obtained were multiplied by the sample dilution ratios (dilution ratio with diluent$\times$1.3) to give the concentrations of the mental stress-related protein in the saliva samples.

10) The detectable concentrations of the protein in the diluted samples ranged from 10 to 200 ng/ml while the detection sensitivity was 2 ng/ml.

ELISA-Biotin/Avidin Technique

The operation steps 1) to 6) of the ELISA-sandwich AP technique as described above were repeated.

7) After washing the plate, a 500-fold dilution of a biotinylated secondary antibody (biotinylated mouse IgG anti-stress-related protein antibody, 1 mg/ml) was added at a ratio of 50 µg/well and the plate was left to stand at 37° C. for 1 hour.

8) After washing the plate, a 500-fold dilution of an enzyme-labeled avidin (alkaline phosphatase-conjugated avidin, Dakopatts cat No. D365) was added at a ratio of 50 µg/well and the plate was left to stand at 37° C. for 1 hour.

The operation steps 7) to 10) of the ELISA-sandwich AP technique as described above were repeated as steps 9) to 12).

13) The detectable concentrations of the protein in the diluted samples ranged from 1 to 50 ng/ml while the detection sensitivity was 0.2 ng/ml.

The method and the diagnostic kit of the present invention makes it possible to easily detect the mental stress-related protein at a high sensitivity, compared with the conventional methods. Thus, the level of unconsciously accumulated mental stress can be measured, which provides possibilities to the prevention of the onset of disorders caused by mental stress or appropriate treatments of these disorders at an early stage.

What is claimed is:

1. A method for assaying a protein which results from certain disorders caused by mental stress in a human body fluid by an immunoassay technique, wherein the immunoassay utilizes an antibody against the protein resulting from certain disorders caused by mental stress, said method comprising the following steps:

contacting a mental stress-related protein with an antibody or fragment thereof, which specifically binds to said protein to form a mixture of antigen-antibody reaction products;

detecting the presence of said antigen-antibody reaction products; and correlating the detected antigen-antibody reaction products with a control standard sample to yield the concentration of mental stress-related protein, wherein said protein or fragment thereof has the following properties:

(1) a molecular weight of about 14 kDa; and
(2) a N-terminal partial sequence represented by SEQ ID NO: 1.

2. The method as claimed in claim 1 wherein said immunological assay technique is the ELISA technique.

3. The method as claimed in claim 1 or 2 wherein said body fluid is saliva.

4. The method of claim 1, wherein the antibody is a polyclonal or monoclonal antibody or fragment thereof.

5. The method of claim 4, wherein the fragment is a binding fragment selected from the group consisting of Fab, F(ab')$_2$ and Fv.

6. The method of claim 1, wherein the detection of said antigen-antibody reaction products is by a technique selected from the group consisting of radioimmunoassay, enzyme immunoassay, immunofluorescence assay, light emission immunoassay, immunoprecipitation and immunoturbidimetry.

7. A kit for diagnosing disorders caused by mental stress, which comprises an antibody against a protein resulting from certain disorders caused by mental stress, wherein said protein or fragment thereof has the following properties:

(1) a molecular weight of about 14 kDa; and
(2) a N-terminal partial sequence represented by SEQ ID NO: 1.

* * * * *